United States Patent
Cassidy et al.

[11] Patent Number: 5,961,501
[45] Date of Patent: Oct. 5, 1999

[54] FLUID CONTAINMENT BAG

[75] Inventors: Clarence A. Cassidy, Carlsbad; Daniel L. Young, Escondido; Terry H. Cassidy, Carlsbad; Ruth E. Young, Escondido; Richard E. Warrick, Encinitas, all of Calif.

[73] Assignee: American Innotek, Inc., San Marcos, Calif.

[21] Appl. No.: 09/004,751

[22] Filed: Jan. 8, 1998

Related U.S. Application Data

[63] Continuation of application No. 08/636,071, Apr. 22, 1996, abandoned.

[51] Int. Cl.$^6$ ..................................................... A61M 1/00
[52] U.S. Cl. ........................ 604/327; 604/317; 604/350; 604/351
[58] Field of Search ................................... 604/317, 322, 604/323, 327, 331, 333, 343, 345, 350, 351, 353

[56] References Cited

U.S. PATENT DOCUMENTS

| | | |
|---|---|---|
| 1,123,951 | 1/1915 | Swanson . |
| 1,458,640 | 6/1923 | Chase . |
| 2,343,678 | 3/1944 | Larkin . |
| 2,640,484 | 6/1953 | Johnson . |
| 2,815,025 | 12/1957 | Fenton et al. . |
| 2,883,985 | 4/1959 | Evans . |
| 3,110,312 | 11/1963 | Wirth . |
| 3,297,152 | 1/1967 | Corella et al. ............................ 206/47 |
| 3,331,421 | 7/1967 | Lambert ..................................... 150/9 |
| 3,346,883 | 10/1967 | Ersek ............................................. 4/1 |
| 3,366,116 | 1/1968 | Huck . |
| 3,403,410 | 10/1968 | Benzel et al. ............................... 4/110 |
| 3,403,715 | 10/1968 | Trudel ....................................... 150/9 |
| 3,405,714 | 10/1968 | Moss . |
| 3,554,368 | 1/1971 | Nagel ...................................... 206/46 |
| 3,556,102 | 1/1971 | Davis . |
| 3,577,989 | 5/1971 | Anderson . |
| 3,597,770 | 8/1971 | Jacuzzi et al. ............................. 4/110 |
| 3,612,133 | 10/1971 | Jarund ......................................... 150/5 |

(List continued on next page.)

FOREIGN PATENT DOCUMENTS

| | | |
|---|---|---|
| 0640455 | 5/1962 | Canada . |
| 0263315 | 4/1988 | European Pat. Off. . |
| 1815038 | 7/1969 | Germany . |
| 2130181 | 1/1972 | Germany . |
| 2936622 | 3/1981 | Germany . |
| 2016929 | 10/1979 | United Kingdom . |
| 1601735 | 11/1981 | United Kingdom . |
| 2092896 | 8/1982 | United Kingdom . |
| 2094265 | 9/1982 | United Kingdom . |
| 2211196 | 6/1989 | United Kingdom ................... 604/343 |
| 2215211 | 9/1989 | United Kingdom . |
| 2227728 | 8/1990 | United Kingdom . |
| 2268882 | 1/1994 | United Kingdom . |
| WO83/02890 | 9/1983 | WIPO . |
| WO92/03994 | 3/1992 | WIPO . |

OTHER PUBLICATIONS

"Introducing Restop the Ultimate Disposable Toilet," product brochure, Star Pioneer Products, Inc., 1985.
"In and Out," *Mega Molecules*, Hans–Georg Elias, 1985, Springer–Verlag.
Advertisement from Sporty's Catalog, 1989, p. 65.
Product brochure for *CareMate Disposable Waste Management System*, Guardian Products, Inc., 1989.
Product Information Bulletin for *SANWET Superabsorbent Polymers*, Hoechst Celanese.

*Primary Examiner*—Mark O. Polutta
*Attorney, Agent, or Firm*—Brown, Martin, Haller & McClain, LLP

[57] ABSTRACT

A fluid containment bag is constructed of three sheets sealed along their perimeters but for a portion defining an opening. Two adjoining sheets define an envelope having a hollow interior into which bodily fluids may be received through the opening for receiving the bodily fluids from a catheter via a flutter valve. A hydrophilic material within the bag gels rapidly upon contact with the bodily fluids in the bag and facilitates closure of the valve.

15 Claims, 2 Drawing Sheets

U.S. PATENT DOCUMENTS

| | | | |
|---|---|---|---|
| 3,672,370 | 6/1972 | Marsan . | |
| 3,797,734 | 3/1974 | Fleury et al. | 229/62.5 |
| 3,865,165 | 2/1975 | Glass | 150/1 |
| 3,920,179 | 11/1975 | Hall | 229/63 |
| 4,122,851 | 10/1978 | Grossner . | |
| 4,173,979 | 11/1979 | Odis . | |
| 4,179,367 | 12/1979 | Barthell et al. | 210/41 |
| 4,305,161 | 12/1981 | Diaz | 4/144.2 |
| 4,387,713 | 6/1983 | Calanni | 604/333 |
| 4,411,659 | 10/1983 | Jensen et al. | 604/332 |
| 4,435,171 | 3/1984 | Goldberg et al. | 604/49 |
| 4,490,145 | 12/1984 | Campbell | 604/333 |
| 4,511,358 | 4/1985 | Johnson, Jr. et al. | 604/327 |
| 4,533,354 | 8/1985 | Jensen | 604/323 |
| 4,541,117 | 9/1985 | Ashbeck | 383/64 |
| 4,581,763 | 4/1986 | Olsen | 383/49 |
| 4,790,834 | 12/1988 | Austin | 604/349 |
| 4,820,291 | 4/1989 | Terauchi et al. | 604/349 |
| 4,909,478 | 3/1990 | Steer | 251/352 |
| 4,938,747 | 7/1990 | Wallace | 604/317 |
| 4,955,879 | 9/1990 | Mervine | 604/327 |
| 5,002,986 | 3/1991 | Fujiura et al. | 524/47 |
| 5,032,118 | 7/1991 | Mason | 604/349 |
| 5,067,821 | 11/1991 | Young | 383/36 |
| 5,193,553 | 3/1993 | Kalinoski | 128/767 |
| 5,234,419 | 8/1993 | Bryant et al. | 604/320 |
| 5,263,946 | 11/1993 | Klug | 604/327 |
| 5,267,989 | 12/1993 | Moyet-Ortiz | 604/349 |
| 5,307,819 | 5/1994 | Trautmann et al. | 128/767 |
| 5,315,960 | 5/1994 | Lamp | 119/95 |
| 5,404,999 | 4/1995 | Bednar | 206/204 |
| 5,409,474 | 4/1995 | Fleeman-Hardwick | 604/349 |
| 5,411,495 | 5/1995 | Willingham | 604/329 |
| 5,417,677 | 5/1995 | Schneider et al. | 604/332 |

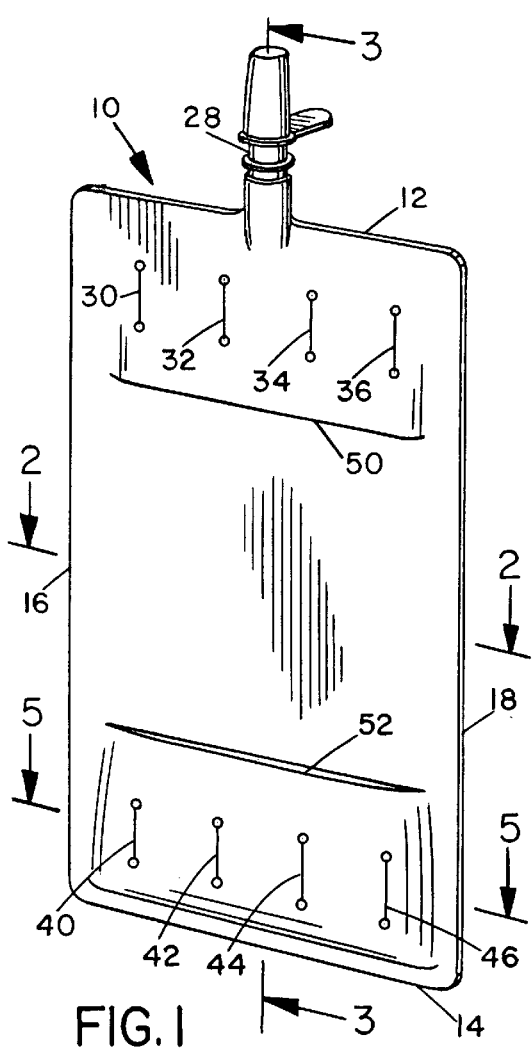
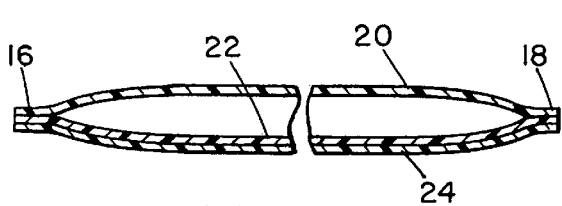
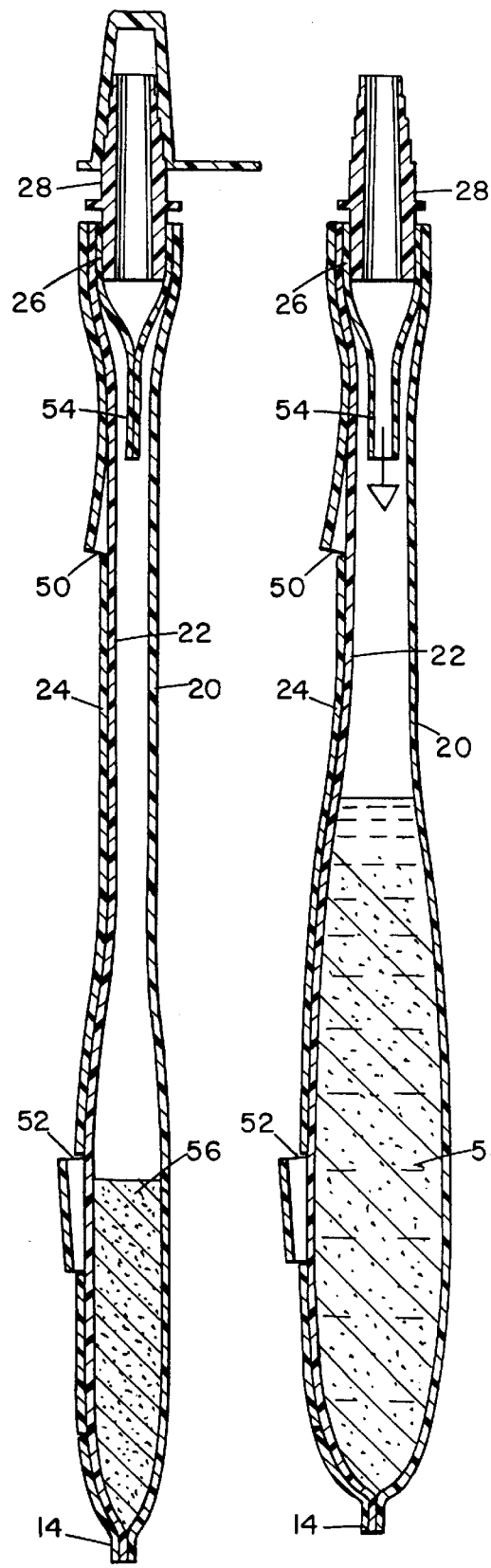
FIG. 1
FIG. 2
FIG. 3
FIG. 4

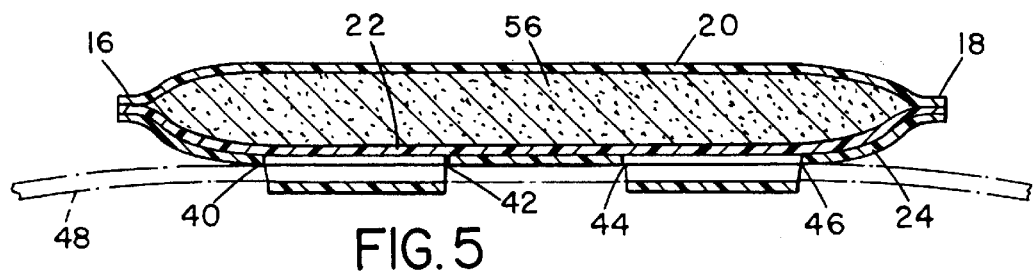
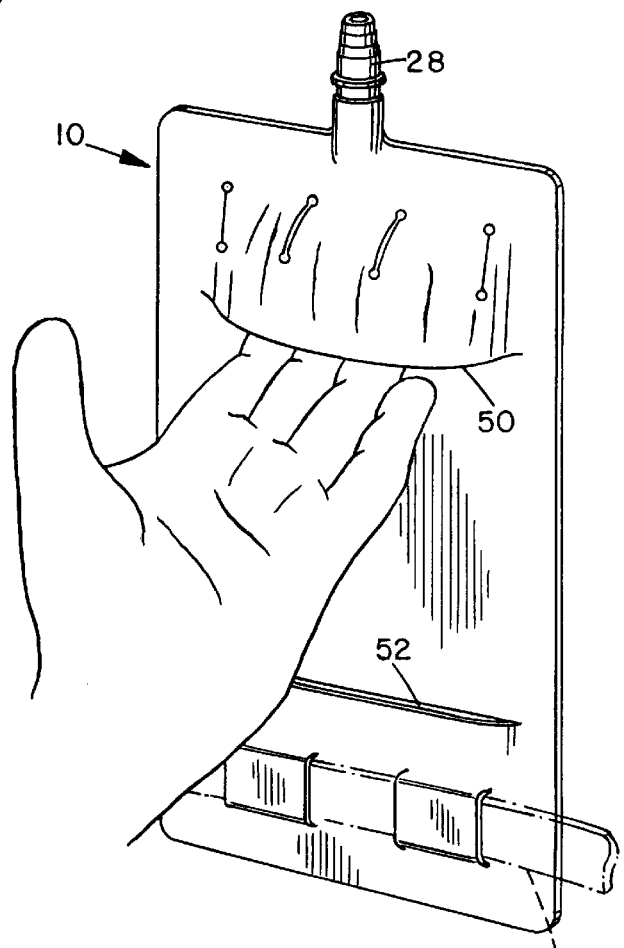
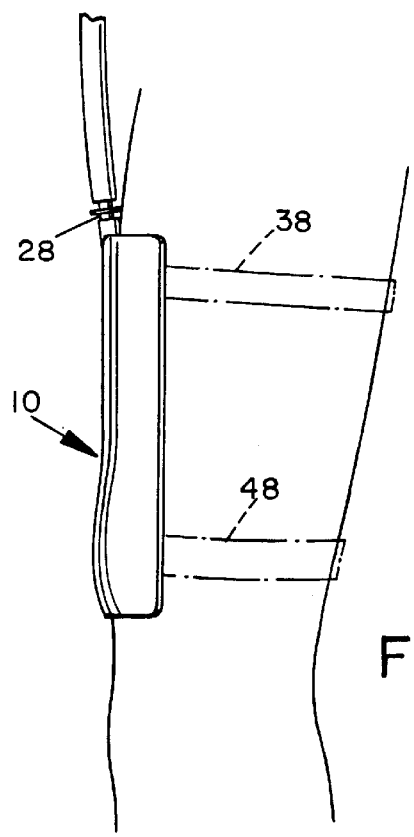

FLUID CONTAINMENT BAG

CROSS-REFERENCE TO RELATED APPLICATIONS

This is a continuation of application Ser. No. 08/636,071, filed Apr. 22, 1996, abandoned.

BACKGROUND OF THE INVENTION

1. Field of the Invention

The present invention relates generally to fluid containment bags and, more specifically, to a disposable bag for collection and containment of human bodily fluids such as urine, feces, or bile via a catheter or other connecting device.

2. Description of the Related Art

Persons who have undergone a colostomy, ileostomy or other surgical procedure involving the digestive tract may use a bag connected via a catheter or other connecting device to the stoma for collecting the effluent. Similarly, incontinent persons may use a bag connected via a catheter to their urinary tracts. Such bags typically have a flattened, rectangular shape with an opening in the top edge for receiving the fluid into the bag. The bag may also include an opening with a controllable valve in the bottom edge for periodically draining the fluid that collects in the bag.

The bag may be secured to the person's leg and concealed beneath clothing while the person moves about or may be suspended from a support while the person sleeps. The bag may include straps for securing it to a person's leg. The straps are typically made of an elastomeric material and looped through slits in a wing area or peripheral area adjacent the top and bottom peripheral edges of the bag.

Practitioners in the art have recognized several problems associated with bodily fluid collection bags. Fluid may slosh about in the bag and annoy or embarrass the wearer. In addition, fluid in the bag may backflow into the catheter, increasing the risk of infecting the wearer. Punctures as small as a pinhole can cause fluid to leak. Furthermore, odors can escape through the same path along which fluid can backflow. Even the plastic walls of certain bags are not sufficiently impermeable to odors to completely prevent their escape.

U.S. Pat. No. 4,179,367, issued to Barthell et al., describes a hydrophilic polymer in granular or powdered form that forms a stiff gel or semisolid when it mixes with a water-based fluid such as urine collected in a bag. Mixing the polymer with collected urine thus prevents it from sloshing. Perfumes or deodorizing chemicals may be mixed with the hydrophilic polymer to mask odors.

A fluid collection bag having a gellable polymer, as suggested by Barthell et al., would be as susceptible to the same backflow problem as a conventional drainable fluid collection bag. The gelled material has a curd-like consistency that is considerably more viscous than bodily fluids and thus does not slosh about. Nevertheless, the gelled material may be undesirably expelled from the bag if the bag is upset or squeezed.

Practitioners in the art have developed drainable fluid collection bags that include a one-way valve at the intake opening to reduce backflow of collected fluids into the catheter if the bag is upset or squeezed. The one-way valve typically consists of a pliable tube that extends into the bag from the intake opening. The tube has a flattened shape when empty of fluid because it has two opposing walls that meet along two seams. Fluid may enter the bag because its pressure spreads apart the opposing walls of the tube. Fluid that has thus collected in the bag closes the valve by pressing the walls of the tube together or against the inside surfaces of the walls of the bag. The tube remains closed until further fluid is introduced. This type of one-way valve is often called a "flutter valve." Examples of bodily fluid collection bags having flutter valves are disclosed in U.S. Pat. Nos. 2,883,985, issued to Evans, 3,331,421, issued to Lambert, 3,403,410, issued to Benzel, et al., and 4,581,763, issued to Olsen. The perimeters of the walls of a flutter valve may, in the closed position, define a rectangular or ribbon shape, such as those disclosed by Olsen and Evans, or a triangular or conical shape, such as those disclosed by Lambert and Benzel, et al. Flutter valves may reduce fluid backflow, but the sealing effect is rather poor and does not completely prevent backflow. Flutter valves may also allow gases and their associated odor to escape.

These problems and deficiencies are clearly felt in the art and are solved by the present invention in the manner described below.

SUMMARY OF THE INVENTION

The present invention includes a disposable bag for collecting bodily fluids that comprises a body including a bag-like envelope defining two surfaces or planes and an opening for receiving bodily fluids, and also including a back portion defining a third surface or plane adjoining one surface of the envelope and having apertures, such as slits or openings, for attaching straps. The bag may further comprise a one-way valve in fluid communication with the opening for preventing backflow of the fluids through the opening. The bag may have any suitable shape and may be formed in any suitable manner, such as by heat-sealing one or more members made of sheet-like flexible plastic.

The body may consist entirely of the bag-like envelope, i.e., without any wing or peripheral area outside the envelope to which straps could otherwise be attached in the conventional manner. Rather, the back portion has apertures, such as slits or larger openings, for attaching straps. The ratio of the interior volume of the bag to the total size or area of the bag is thus maximized because the apertures for receiving the straps are entirely within the periphery of the back portion, thereby not detracting from the area of the envelope. The bag can thus hold a greater amount of fluid and be manufactured more economically than prior bags of equal total size or area. Furthermore, the straps do not apply a lateral force across the envelope because they are threaded through the back portion only. Because tension across the envelope is minimized, the envelope is less likely to burst or otherwise fail when full than prior bags.

The envelope may comprise two layers or sheets of flexible plastic that are joined all along their peripheries with the exception of an area defining the opening. The back may comprise a third layer or sheet of plastic that is joined along at least a portion of its periphery to the envelope. Preferably, however, the third layer is joined all along its periphery to the peripheries of the other two layers, with the exception of the area defining the opening. The third layer has apertures, such as slits or larger openings, for receiving straps.

A gellable hydrophilic material may be disposed within the envelope. The hydrophilic material gels rapidly upon contact with the bodily fluids when the bodily fluids are deposited in the bag. The one-way valve opens in response to entry of fluid into it and closes in response to the backflow of fluid or gelled material that has passed through it. The one-way valve may comprise a flutter valve, which is disposed at least partially within the envelope. The gel improves the operation of the flutter valve over conventional flutter valves that are actuated by liquid alone by maintaining the valve more securely in a closed position. The relatively dense gel presses the flutter valve walls together or against the inside surface of the envelope. The cooperation of the gelled material and the flutter valve completely sequesters the material in the bag.

The hydrophilic material may comprise a polymer. The envelope may contain a mixture, including the hydrophilic material and other materials, such as enzymes, deodorants, fragrances, or human body abnormality indicators and/or pregnancy indicators. The material may be in any of a variety of physical forms, such as powder, granules, fibers, mats or foam.

The foregoing, together with other features and advantages of the present invention, will become more apparent when referring to the following specification, claims, and accompanying drawings.

BRIEF DESCRIPTION OF THE DRAWINGS

For a more complete understanding of the present invention, reference is now made to the following detailed description of the embodiments illustrated in the accompanying drawings, wherein:

FIG. 1 is a rear perspective view of the fluid containment bag;

FIG. 2 is an enlarged sectional view taken on line 2—2 of FIG. 1;

FIG. 3 is an enlarged sectional view taken on line 3—3 of FIG. 1;

FIG. 4 is a view similar to FIG. 3, showing the gelling action when liquid is added;

FIG. 5 is an enlarged sectional view taken on line 5—5 of FIG. 1;

FIG. 6 is a view similar to FIG. 1, showing the attachment of a retaining strap and the method of holding the bag; and FIG. 7 illustrates the bag secured to a wearer's leg.

DESCRIPTION OF A PREFERRED EMBODIMENT

As illustrated in FIG. 1, a fluid containment bag of the present invention includes a body 10 that preferably has a generally rectangular perimeter defined by upper and lower edges 12 and 14, respectively, and side edges 16 and 18, respectively. Body 10 is constructed of three sheets or layers 20, 22, and 24 that join one another along edges 12, 14, 16 and 18 of body 10. Layers 20, 22 and 24 are preferably made of lightweight flexible plastic, such as polyethylene, vinyl, mylar, or the like. The plastic should be fluid-impermeable and sufficiently thick and tough to resist accidental puncture under normal handling. With the exception of an area defining an opening 26 in upper edge 12 of body 10, layers 20, 22 and 24 are preferably heat-sealed to one another all along edges 12, 14, 16 and 18. Layers 20 and 22 together define a bag-like envelope. Layer 24 defines a back of body 10. A barbed connector 28 for attaching a catheter is disposed in opening 26. The envelope preferably has a capacity to hold on the order of between ten to twenty fluid ounces (300–600 cc) of bodily fluids.

Layer 24 has four upper vertical slits 30, 32, 34 and 36 for receiving an upper strap 38 and four lower vertical slits 40, 42, 44 and 46 for receiving a lower strap 48, as shown in FIGS. 5–7. Straps 38 and 48 may be used to fasten the bag to a user's leg, as shown in FIG. 7. Layer 24 also has an upper horizontal slit 50 and a lower horizontal slit 52. Horizontal slits 50 and 52 allow a user's fingers access to a portion of the space between layers 22 and 24 to facilitate threading straps 38 and 48 through slits 30–36 and 40–46, respectively. Horizontal slits 50 and 52 also provide a convenient means for a user to grip the bag while fastening it to or removing it from the user's leg, as shown in FIG. 6. It should be understood that the terms "vertical" and "horizontal" are used herein to describe the two mutually perpendicular orientations of the slits with respect to the bag, and do not refer to orientations of the slits with respect to the Earth.

It should be noted that, although in the illustrated embodiment layer 24 is coextensive with layers 20 and 22, in other embodiments layer 24 may cover an area smaller than that covered by layers 20 and 24. Similarly, although in the illustrated embodiment layer 24 is heat-sealed to layers 20 and 22 along all portions of edges 12, 14, 16, and 20 with the exception of the area defining opening 26, in other embodiments layer 24 may be joined to the envelope along only a portion of edges 12, 14, 16 and 20. Layer 24 may thus comprise two or more portions, each joined to the envelope but separated from each other by a portion of edges 12, 14, 16 and 20 where layer 24 is not joined to the envelope. The opening or aperture between such portions may be used as a grip during fastening and removal of the bag in the same manner as the slits described above.

The fluid containment bag also includes a flutter valve 54 inside the envelope and connected to the lower end of connector 28. Flutter valve 54 comprises a tube of flexible plastic material that assumes a flattened or ribbon-like shape when in the closed position. As shown in FIG. 4, when fluid enters flutter valve 54 through connector 28, the opposing walls spread open to admit the fluid. When all fluid has exited flutter valve 54, the opposing walls close in response to the resiliency of the opposing walls. In the closed position, opposing walls of flutter valve 54 are in contact with each other, thereby preventing fluid in the envelope from flowing back into connector 28. Furthermore, the pressure exerted on the flutter valve by the fluid itself maintains it in the closed position.

As shown in FIG. 3, enclosed within the envelope and critical to the function of the present invention is a quantity of a gellable material 56 for transforming the fluid entering the bag into a gelatinous or semi-solid state.

Gellable material 56 contains a hydrophilic polymer that gels very rapidly (normally within 30 seconds, and often much less than that) upon contact with water-based liquids. Such polymers are commercially available and are commonly found in a variety of known products, including disposable diapers and cleaning compositions. Typical examples include the acrylonitrile-based polymers described in Elias, *Mega Molecules*, pp. 157–158 (1987) and the acrylic polymers described in U.S. Pat. No. 4,179,367 (Barthell et al.). Gellable material 56 is preferably a complex mixture including not only the gellable polymer but also a material such as a protease enzyme to attack and break down the urine, blood or other bodily fluid to enhance the operation of the gellable polymer. Deodorants, fragrances, biocides, and antiviral substances may also be included in gellable material 56. Gellable material 56 may by in any convenient physical form that can be placed into the envelope; granular, powdered, foamed, matted, woven and fibrous forms are all suitable. The inventors of the present invention have successfully used a granular material commercially available under the trade name "Sanwet IM-5600" from Hoechst Celanese, Superabsorbent Material Division, of Portsmouth, Va. which is described as containing a starch grafted sodium polyacrylate. This product is a proprietary product and the exact identification of the components and formula is not available to the inventors of the present invention. In tests, the product has shown the property of gelling and sequestering all bodily fluids placed into test bags within no more than twenty seconds.

The particle sizes of the granulated material can be within a fairly wide range, but preferably will have at least about 80%, more preferably 80%–90%, in the range of −40+120 mesh U.S. Sieve Series (74–240 µm). It has been found that within this range, and more preferably with at least about 50% in the range of −40+80 mesh (177–240 µm), the liquid absorbency rate is maximized. If a large proportion of the granules are smaller than 120 mesh, there will be a tendency for the material to dust unduly in handling and storage prior to use and to restrict liquid flow throughout the material during use, while if there is a large proportion with particle sizes larger than 40 mesh, the rate of liquid absorption will be slowed. A typical analysis will be 8% +40 mesh, 66% −40+80 mesh, 19% −80+120 mesh and 7% −120 mesh. It is believed that the particle size is instrumental in achieving the rapid gellation time.

When fluid enters the envelope, flutter valve 54 not only immediately prevents it from flowing back into connector 28, but it thereafter prevents the gelled material 58 from flowing back into connector 28, as shown in FIG. 4.

Flutter valve 54 thus performs two sequential functions to essentially completely prevent escape of fluid from the envelope. The likelihood of gelled material 58 escaping is minimized because gelled material 58 is too viscous or dense to penetrate the closed lower end of flutter valve 54. Moreover, when the bag is upset or shaken, the shifting gelled material 58 tends to press flutter valve 54 against the wall of the envelope to a greater extent than a liquid.

It will be evident that there are numerous embodiments of the present invention which, not specifically described above, are clearly within the scope and spirit of the invention. Consequently, the above description is considered to be exemplary only and the full scope of the invention is to be determined solely by the appended claims.

What is claimed is:

1. A bodily fluid collection bag, comprising:
a first layer made of sheet-like plastic and having first and second side edges, a top edge and a bottom edge;
a second layer made of sheet-like plastic and having first and second side edges, a top edge and a bottom edge, said first side edge of said first layer joined to said first side edge of said second layer, said second side edge of said first layer joined to said second side edge of said second layer, said bottom edge of said first layer joined to said bottom edge of said second layer, and a portion of said top edge of said first layer joined to a portion of said top edge of said second layer with unjoined portions of said top edges of said first and second layers defining an opening for receiving fluid, said first layer not joined to said second layer except at said edges, said edges of said first and second layers joined to one another defining an envelope having an interior that is completely sealed but for said opening to sequester fluid in said envelope; and
a third layer made of sheet-like plastic exterior to said envelope and having first and second side edges, a top edge and a bottom edge, said first side edge of said third layer joined to said first side edge of said second layer, said second side edge of said third layer joined to said second side edge of said second layer, said bottom edge of said third layer joined to said bottom edge of said second layer, and said top edge of said third layer joined to said top edge of said second layer, said third layer not joined to said second layer except at said edges.

2. The bodily fluid collection bag recited in claim 1, wherein said first, second and third layers are made of identical sheets of plastic.

3. The bodily fluid collection bag recited in claim 1, wherein said third layer has a plurality of slits.

4. The bodily fluid collection bag recited in claim 3, wherein two of said slits are oriented parallel to said side edges of said third layer for receiving a strap.

5. A bodily fluid collection bag, comprising:
a body having a periphery, said body consisting of a back and an envelope for containing fluid, said envelope having a periphery, a hollow interior and an opening for receiving fluid, said back having a periphery and a plurality of apertures, said plurality of apertures not extending through said envelope said back connected along at least a portion of its periphery to at least a portion of said periphery of said envelope, said back not extending beyond said periphery of said envelope; and
a one-way valve in fluid communication with said opening.

6. The bodily fluid collection bag recited in claim 5, wherein said apertures include a vertical slit for receiving a strap.

7. The bodily fluid collection bag recited in claim 5, wherein said apertures include a horizontal slit for providing a grip.

8. The bodily fluid collection bag recited in claim 5, wherein said periphery of said back is coextensive with said periphery of said body.

9. The bodily fluid collection bag recited in claim 5, wherein said envelope comprises of two sheets of plastic joined to one another along said periphery of said body.

10. The bodily fluid collection bag recited in claim 5, wherein said back comprises a sheet of plastic joined to said envelope.

11. A bodily fluid collection bag, comprising:
an envelope for containing fluid, said envelope having first and second side edges, a top edge and a bottom edge, said edges of said envelope together defining a periphery of said envelope, said envelope having a hollow interior and an opening at said top for receiving fluid;
a back having a first side edge and a second side edge, said first side edge of said back connected to said first side edge of said envelope, said second side edge of said back connected to said second side edge of said envelope, said back having at least two apertures between its first and second side edges said at least two apertures not extending through said envelope; and
a strap extending through said two apertures in said back.

12. The bodily fluid collection bag recited in claim 11, wherein said apertures include a horizontal slit for providing a grip.

13. The bodily fluid collection bag recited in claim 11, wherein said periphery of said back is coextensive with said periphery of said body.

14. The bodily fluid collection bag recited in claim 11, wherein said envelope comprises of two sheets of plastic joined to one another along said periphery of said body.

15. The bodily fluid collection bag recited in claim 11, wherein said back comprises a sheet of plastic joined to said envelope.

* * * * *